United States Patent [19]

McCune, III

[11] Patent Number: 5,639,939
[45] Date of Patent: Jun. 17, 1997

[54] CHIMERIC IMMUNOCOMPROMISED MAMMAL COMPROSING VASCULARIZED FETAL ORGAN TISSUE

[75] Inventor: Joseph M. McCune, III, San Francisco, Calif.

[73] Assignee: The Board of Trustees for the Leland Stanford Junior University, Palo Alto, Calif.

[21] Appl. No.: 205,053

[22] Filed: Mar. 1, 1994

Related U.S. Application Data

[63] Continuation-in-part of Ser. No. 737,882, Jul. 25, 1991, abandoned, which is a continuation of Ser. No. 343,797, Apr. 26, 1989, abandoned, which is a continuation-in-part of Ser. No. 287,075, Dec. 20, 1988, abandoned, which is a continuation of Ser. No. 137,173, Dec. 23, 1987, abandoned.

[51] Int. Cl.$^6$ ............................................. A61K 49/00
[52] U.S. Cl. .................. 800/2; 800/DIG. 5; 623/11; 424/9.2; 424/553; 424/578; 424/579; 424/93.7; 424/577; 424/549; 424/582; 424/580
[58] Field of Search ........................ 800/2, DIG. 5; 623/11; 424/9.2, 93.7, 580, 553, 578, 579, 577, 549, 582

[56] References Cited

PUBLICATIONS

G. Bastert, et al. (1977) Endocrinology 101:365. Heterotransplantation of human fetal pituitaries in nude mice.
K. Usadel, et al. (1977) Lancet, Feb. 12:365. Human fetal pancreas transplants in nu/nu mice.
B. Tuch, et al., (1984) Diabetes 33:1180. Histologic differentiation of human fetal pancreatic explants transplated into nude mice.
P. Groscurth and G. Tondury (1982) Analytical Embryology 165:291. Cytodifferentiation of human fetal lung tissue following transplantation into nude mice.
I. Fohlmeister and O. Hohentanner (1985) Nat. Immun. Cell Growth Regul. 4:221–228. The possibility of assaying Wistar rat bone marrow CFUs in a xenogeneic (rat to mouse) system.
A. Wade, et al. (1987) Transplatation 44:88–92. Characterization of xenogeneic mouse–to–rat bone marrow chimeras.
C. Povlsen, et al. (1974) Nature 248:247–249. Heterotransplantation of human foetal organs to the mouse mutant *nude*.
F. Yin and N. Lomax (1986) J. Gen. Virol. 67:2335–2340. Establishment of a mouse model for human rhinovirus infection.

S. Kamel–Reid and J. Dick (1988) Science 242:1706–1709. Engraftment of immune deficient mice with human hematopoietic stem cells.
I. Lubin, et al. (1991) Science pp. 427–430. Engraftment and development of human T and B cells in mice after bone marrow transplantation.
O. Taguchi, et al., (1986) J. Exp. Med. 164:60–71. Development of multiple organ–localized autoimmune diseases in nude mice after reconstitution of T cell function by rat fetal thymus graft.
S. Kyozumi, et al., (1992) Blood 79:1704–1711. Implantation and maintenance of functional human bone marrow in SCID–hu mice.
P. Mombaerts, et al. (1992) Cell 68:869–877. RAG–1–deficient mice have no mature B and T lymphocytes.
T. Kollman, et al. (1993) J. Exp. Med. 177:821–832. The concurrent maturation of mouse and human thymocytes in human fetal thymus implanted in NIH–beige–nude–xid mice is associated with the reconstitution of the murine immune system.
Bosma (1983) Nature 301:527–530. A severe combined immunodeficiency mutation in the mouse.
G. Yancopoulos and F. Alt (1988) Science 241:1581–1583. Reconstruction of an immune system.
W. Murphy, et al., (1987) J. Exp. Med. 165:1212–1217. Rejection of bone marrow allografts by mice with severe combined immune deficiency (SCID).
J. Sacci, et al. (1992) P.N.A.S. 89:3701–3705. Mouse model for exoerythrocytic stages of *Plasmodium falciparum* malaria parasite.
G. Fulop and R. Phillips (1986) J. of Immun. 136(12):4438–4443. Full Reconstitution of the Immune Deficiency in scid Mice with Normal Stem Cells Requires Low Dose Irradiation of the Recipients.

*Primary Examiner*—Jasemine C. Chambers
*Assistant Examiner*—Jill Schmuck
*Attorney, Agent, or Firm*—Pamela J. Sherwood; Fish and Richardson P.C.

[57] ABSTRACT

Xenogeneic tissue is introduced into an immunocompromised host for interacting with agents and using such interaction for evaluating efficacy of drugs and vaccines, producing xenogeneic monoclonal antibodies, evaluating the effect of the various agents on specific tissues and the like. Particularly, drugs can be evaluated for their efficacy against a wide variety of pathogens which infect xenogeneic tissue, agents can be evaluated for their effect on the xenogeneic immune system and monoclonal antibodies to a predetermined epitope may be produced.

35 Claims, No Drawings

CHIMERIC IMMUNOCOMPROMISED MAMMAL COMPROSING VASCULARIZED FETAL ORGAN TISSUE

CROSS-REFERENCE TO RELATED APPLICATIONS

This application is a continuation-in-part of application Ser. No. 07/737,882, filed Jul. 25, 1991, now abandoned which is a continuation of application Ser. No. 07/343,797, filed Apr. 26, 1989 now abandoned, which is a continuation-in-part of application Ser. No. 07/287,075, filed Dec. 20, 1988, now abandoned which is a continuation of application Ser. No. 07/137,173, filed Dec. 23, 1987 now abandoned.

This invention was made with Government support under NIH Grant no. CA 03352. The Government has certain rights in this invention.

INTRODUCTION

1. Technical Field

The field of this invention is immunocompromised mammals comprising xenogeneic tissue and their use with interactive agents.

2. Background

The field of medicine for the treatment of humans has depended for the most part on animal model systems where the tissue involved was the animal tissue. These model systems have frequently involved pathogenic agents which had a broad host range including human and other mammalian hosts, pathogenic agents which were capable of causing disease in the animal model which were analogous to a pathogenic agent capable of causing disease in humans or caused diseases in animals which were etiologically and symptomatically analogous to the disease in humans and the like. There are many shortcomings with these techniques. Since the cells and tissue which are involved with the pathogens are not human tissue, and they may differ in a wide variety of ways in their response from the response of human tissue, there is always the uncertainty as to whether the animal cells provide a reasonable predictor of what may be anticipated in a human. Also, with many genetic diseases, the same lesion in an animal may have a significantly different effect in humans.

There is also interest in being able to understand how human cells respond to various stimuli, how different types of cells interact, within the bone marrow, such as stromal endothelium cells and bone marrow, lymphoid and myeloid cells, and the like.

Having viable human tissue in an animal model system provides for numerous advantages. One can investigate the effect of various agents on the tissue at various stages in the development of the cells and the tissue. In addition, one can investigate the interaction of cells and secreted agents on tissue, as well as the communication between various tissues and the feedback and regulation of the metabolism of the cells. Importantly, one may introduce various agents, both natural and synthetic, into the host to determine the effect of the agents on the tissue, its metabolism, proliferation and differentiation. In addition, one may use combinations of the reagents, such as pathogens and drugs, to determine the effect of the pathogen on the tissue and the effect of the drug on the pathogen and the tissue.

It is therefore of substantial interest to develop and provide mammalian model systems comprising human tissue, which remains viable for extended periods of time, is responsive to various agents and permits the use of techniques which allow for the investigation of the changes in the tissue, the etiology of disease and the effect of agents on pathogens and tissue for prophylaxis and therapy. Thus, there is a need for an animal model which allows for study of both physiological and pathophysiological conditions and agents which can modulate such conditions.

Relevant Literature

References concerned with immunoincompetent hosts, particularly CID or SCID hosts, include McGuire et al., *Clin. Immunol. and Immunopath.* (1975) 3:555–566; Perryman and Torbeck, *J. Am. Vet. Med, Assoc.* (1980) 176:1250–1251; Shultz and Sidman, Genetically-determined Murine Models of Immunodeficiency, The Jackson Laboratory, Bar Harbor, ME; Bosma et al., *Nature* (1983) 301:527–530; Custer et al., *Amer. J. Path.* (1985) 120:464–477; Dorshkind et al., *J. of Immunol.* (1985) 134:3798–3801; Kerghtley et al., *Lancet*, Nov. 1, 1975, 850–853; Touraine, *Immunological Rev.* (1983) 71:103–121; and Fulop and Phillyes, *J. of Immunology* (1986) 136:4438–4443.

References concerned with xenogeneic cells growing within live hosts include Krueger et al., *Proc. Natl. Acad. Sci. USA* (1983) 80:1650–1654; Krueger and Shelby, *J. Inv. Dermatol.* (1981) 76:506–510; Ware et al., *J. Immunol Meth.* (1985) 85:353–361; Ford et al., *Nature* (1956) 177:452–454; Povlsen, et al., *Nature* (1974) 248:247–249; Mannhardt et al., *Thymus* (1982) 4:209–220; Schulte-Wisserman et al., *Scand. J. Immunol.* (1978) 8:387–396. Please specifically note, McCune et al., *Science* (1988) 241:1632–1639 and the comment therein; Yancopoulos and Alt, *Ibid* (1988) 241:1581–1583, and references cited therein.

See also EPA 0 322 240.

SUMMARY OF THE INVENTION

Methods, non-human mammals and organs are provided for initiating cellular and/or tissue response under conditions where the response may be evaluated to determine the efficacy of the agents and/or conditions, both prophylactic and therapeutic, to produce products such as immunoglobulins, and to investigate cellular and tissue response to various agents and conditions. The non-human mammals are characterized by being immunocompromised, having a viable, xenogeneic organ or tissue capable of functioning at least in part as the organ or tissue from which it is derived, which tissue is vascularized, and, as appropriate, connected with lymphatic vessels.

DESCRIPTION OF THE SPECIFIC EMBODIMENTS

Methods, compositions and organisms are provided where the organisms are characterized by having solid xenogeneic tissue, normally human tissue, in a non-human viable host where the solid tissue is viable, functional and able to respond to various stimuli, allowing for the analysis of response, the harvesting of products, and the investigation of various physiological processes. In particular, model systems are provided for pathogenesis and hematopoiesis.

The solid implants are able to function for long periods of time, usually in excess of two weeks, more usually in excess of four weeks, and depending upon the particular implant, the site of the implant, the tissue, which may include a variety of cells, including hematopoietic, stromal, lung, fibroblasts, epithelium, endothelium, neurons, stem cells, or other cells associated with particular solid organs, such as bone marrow, pancreas, appendix, tonsil, gut, lung, GALT (gut-associated lymphoid tissue), MALT (mucosa-associated lymphoid tissue), tongue, mucosal tissue, adrenal gland, thymus, liver, central nervous system tissue, spinal cord, thyroid, pituitary gland, hypothalamus, bone, including osteoclasts and osteoblasts, muscle, including myoblasts, myocytes, neuronal tissue and the like.

Among the organs and cells associated with hematopoiesis are stem cells (precursor cells for the various human hematopoietic lineages, e.g., lymphoid, myelomonocytic and erythroid) and cells providing a processing organ, such as the thymus, bone marrow, spleen, lymph node, tonsils, appendix and skin. Cells of interest associated with the hematopoietic system include monocytes, macrophages, B-cells, T-cells, neutrophils, erythrocytes, eosinophils, megakaryocytes, platelets, dendritic cells, natural killer cells, cytotoxic T-lymphocytes (CTLs), tumor-infiltrating lymphocytes (TILs), helper cells (CD4), suppressor cells (CD8), lymphocyte-activated killer cells (LAKs), antibody dependent cytotoxic cells (ADCC), and the like.

A wide variety of tissues may find use and be able to grow in the subject host. In addition, the tissues may be subject to induction of disease or may be available in their diseased form. The following table provides a list of tissues of interest with various pathologic conditions associated with such tissue.

TABLE 1

| Tissue | Pathologic Condition |
| --- | --- |
| Connective tissue | Rheumatic fever, systemic lupus erythematosus, rheumatoid arthritis, gout |
| Brain (nerve) tissue | Paralysis, Alzheimer's disease, multiple sclerosis, Lou Gehrig's disease, glycogenesis |
| Synovial tissue | Rheumatoid arthritis |
| Respiratory tissue | Emphysema, edema, Goodpasture's syndrome, sarcoidosis |
| Liver | Cirrhosis, Wilson's disease, Pompe's disease, Forke's disease, hepatitis, primary biliary cirrhosis, alpha$_1$-antitrypsin disease, hemochromatosis, glycogeneses |
| Kidney | Glomerulonephritis, pyelonephritis, lupus nephritis, tubular acidosis, ketoacidosis, renal failure, cystinuria |
| Thyroid | Hypothyroidism, hyperthyroidism, Grave's disease, goiter, Hashimoto's disease |
| Colon | Peptic ulcer, stomach or duodenum, diverticulosis, inflammatory bowel disease |
| Skin | Ulcer, gangrene, psoriasis, erythroderma syndrome, pemphigus pemphigoid |
| Lymph node | Lymphadenopathy, lymphoma |
| Blood vessels | Vasculitis, Wegener's granulomatosis, giant cell vasculitis, polyarteritis nodosa |
| Pancreas | Diabetes, pancreatitis |
| Breast | Carcinoma 1° or 2° |
| Pineal Gland | Circadian rhythms |
| Prostate | Hypertrophy, CA |
| Testes | Hypogonadism |
| Ovary | Turner's syndrome, Stein-Leventhal syndrome, cyst |
| Reticuloendothelium | Gaucher's disease, Letterer-Siwe disease |
| Stomach | Peptic ulcer, gastritis, pernicious anemia, ulcerative colitis |
| Salivary gland | Sjögren's disease |
| Muscle | Myasthenia gravis, polymyositis, muscular dystrophy |
| Parathyroid | Primary hypoparathyroidism |
| Adrenal gland | Addison's disease, Cushing's disease, Conn's disease |

In other situations, it may be of interest to study the pathogenesis of various infectious agents and/or the effect of various drugs or treatments on the induction or progress of the disease. The following table provides a list of infectious agents of interest and tissue which may find application in the study of these various infectious agents. The table is not intended to be exhaustive, and in some instances, one tissue will be preferred over another tissue in relation to a particular agent. Furthermore, there may be situations where a tissue which is not listed as employed, because of availability of such infected tissue, level of viability of the tissue in the host, and the like.

TABLE 2

| Infectious Agents | Human Tissue |
| --- | --- |
| Gram-negative bacteria | Lung, kidney, myocardium, capillaries (endothelium) |
| Pneumococcus | Lung (alveolar walls), trachea |
| Staphylococcus | Integument, long bones, endocardium, myocardium, liver, spleen, brain |
| Streptococcus | Pharynx, mucosal tissue, tonsil, skin, sinus |
| Meningococcus | Pharynx, mucosal tissue |
| Gonococcus | Urethra, vulva |
| Enteric gram-negative bacilli | Lung |
| E. coli | Urethra, appendix, mucosal tissue |
| Klebsiella-Enterobacter-Serratia | Lung, pharynx, urethra |
| Proteus | Skin, bone, urethra |
| Pseudomonas | Skin, urethra, lung |
| Salmonella | Gut, spleen |
| Shigella | Gut |
| Hemophilus | Mucosal tissue, pharynx, tonsil |
| Yersinia | Lymph node |
| Listeria | Skin, liver, spleen, adrenal gland |
| Corynebacterium | Membrane, mucosal tissue, tonsil, pharynx |
| Vibrio (cholera) | Mucosal tissue, gut |
| Clostridium (tetanus) | Skin |
| Clostridium (botulism) | Gut, mucosal tissue |
| Mycobacterium (tuberculosis) | Lung, lymph node |
| Mycobacterium (leprosy) | Skin, nerves, respiratory mucosa |
| Treponema (syphilis) | Mucosal tissue |
| Histoplasma | Skin, lung |
| Candida | Mucosal tissue |
| Mycoplasma | Bronchia, pharynx, trachea, mucosal tissue |
| Chlamydia | Conjunctive, cornea |
| Viruses | |
| HIV | Thymus, lymph nodes |
| Coxsackie, Echo, Reo | Enteric viruses: Muscle, viscera, kidney, mucosal tissue |
| Respiratory viruses: | Mucosal tissue, bronchia, pharynx |
| Rhino, adeno, RSV, parainfluenza, corona | |
| Influenza virus | Respiratory tissue, mucosal tissue |
| Picorna (poliomyelitis) | Pharynx, gut |
| Rhabdovirus (rabies) | Muscle, nerve tissue, brain |
| Slow virus | Brain |
| Measles (rubeola) | Conjunctive, mucosa |
| Rubella | Pharynx, mucosal tissue |
| Smallpox | Pharynx, mucosal tissue |
| Herpes: | |
| Zoster | Pharynx, mucosal tissue |
| Simplex I and II | Respiratory tissue, conjunctive, labia, ganglia, brain |
| EBV | Lymph node, thymus, spleen |
| Mumps (paramyxovirus) | Lymph node, mucosal tissue, meninges |
| Cytomegalovirus | Lymph node, thymus, bone marrow, epithelial tissue |

Among classes of viruses which may be studied are picornaviridae, enteroviruses, rhinoviruses, hepatitis viruses, caliciviridae, Norwalk group, togaviridae, flaviviridae, alphaviruses, rubella, coronaviridae, rhabdoviridae, filoviridae, paramyxoviridae, parainfluenza viruses, mumps virus, measles virus, respiratory syncytial virus, orthomyxoviridae, bunyaviridae, arenaviridae, reoviridae, rotaviruses, lentivirus, orbiviruses, retroviridae, T-cell leukemia viruses, human immunodeficiency viruses, lentiviruses, papovaviridae, polyoma viruses, papilloma viruses, adenoviridae, parvoviridae, herpesviridae, herpes simplex viruses, Epstein-Barr virus, cytomegalovirus, Varicella-Zoster virus, poxviridae, hepadnaviridae, hepatitis viruses A, B and C, and such additional viruses or strains which particularly have human tropism.

In addition, one may choose to use normal tissue which has been subjected to a treatment which allows the normal tissue to mimic human tissue involved with a pathological condition. In this manner, one may provide for various models which would permit the investigation of pathological conditions in tissue. Thus, one may induce hypoxia, lesions, ulcerations, cells which provide cell mediated degeneration, e.g., T-cells, neutrophils, killer cells, etc., genetic diseases by transfection with genetically modified viruses to provide for or inhibit a genetic capability, administrations of toxins, inducing stress, and the like. The list is not intended to be exhaustive, but indicates a variety of tissues which may be used, where pathologic conditions may be induced by various means.

TABLE 3

| Tissue | Pathologic Condition |
| --- | --- |
| Heart | Infarction, hypertension, stenosis, ischemia |
| Vascular system | Vessel wall abnormalities, atherosclerosis, thromboembolism |
| Lymphatic system | Homing (inflammatory), reperfusion injury |
| Pancreas | Diabetes |
| Synovia | Arthritis |
| Lung | Asthma, mineral dust, ARDS |
| Kidney | Glomerulonephritis |
| Gut | Homing (inflammatory), ulcer, nutrient absorption |
| Liver | Bilirubin turnover, cirrhosis, hepatitis (acute toxic exposure) |
| Bone marrow | Anemia |
| Brain and CNS | Multiple sclerosis, myasthenia gravis, Alzheimer's disease |
| Muscle | Muscular dystrophy |
| Bone | Osteoporosis |
| Joint | Tendinitis, bursitis, arthritis, ankylosing spondylitis |

In many instances, it may be desirable to have more than one type of tissue, for example, where one wishes to study the effect of an agent on the immune system or a subset of the immune system, while at the same time studying its efficacy against a pathogen. Thus, in addition to implants or grafts not associated with lymphoid tissue, one may also wish to introduce lymphoid tissue to provide for a response, either cellular or humoral. Hematopoietic stem cells may be introduced into the host in conjunction with embryonic yolk sac, fetal liver, thymus, spleen or lymph node tissue, fetal or adult bone marrow tissue, pancreatic tissue, appendix tissue, tonsil tissue and the like. Other stem cell systems may be employed. In other than the hematopoietic system, combinations may include stem cells of the central or peripheral nervous system, such as neuronal or matrix cells of the fetal central nervous system, spinal cord neurons and the spinal cord, organs of the endocrine system, such as beta-cells and other cells of the islets and pancreas, the adrenal gland, the thyroid gland, and the hypothalami-pituitary axis. The stem cells will be introduced in combination with the appropriate organs in which each of them is induced to differentiate and to become functional.

In some instances, it will be desirable to enhance the proportion of human cells in the peripheral blood, providing for human cells being at least one percent, preferably at least five percent, of the total circulating blood cells. The host bones, in whole or in part, may be irradiated or treated with cytotoxic drugs at a level which will at least partially ablate the endogenous hematopoietic cells. With each type of host, the particular level of treatment may be selected by screening for the level of hematopoietic cells remaining and the proportionate number of viable hosts. Instead of x-irradiation, various cytotoxic drugs may be employed, such as immunotoxins. The bone marrow, as bone or dispersed, will usually be fetal bone marrow and may be employed as chunks, slices, fragments or the like, the size of the bone depending on the size of the host. For a mouse, the bone will generally be less than about 2 cm, more usually less than about 1 cm, providing a total volume of bone of from about 40 to 1200 mm$^3$. The site of introduction of the bone may be intraperitoneal, subcutaneous, mammary fat pad or the like.

Immunocompromised mammalian hosts having the desired immune incapacity exist or can be created. The significant factor is that the immunocompromised host is incapable naturally or in conjunction with the introduced organs to be able to mount an immune response against the xenogeneic tissue or cells. Therefore, it is not sufficient that a host be immunocompromised, but the host may not be able to mount an immune response after grafting, as evidenced by the inability to produce competent B-cells, particularly plasma cells, and/or T-cells, particularly CD4$^+$ and/or CD8$^+$ T-cells. Hosts which are presently available include hosts which have a severe combined immunodeficiency, known as scid/scid.

The SCID hosts lack functional syngeneic B-cells and/or T-cells. In the SCID mouse, the genetic defect appears to be a non-functioning recombinase, for the germline DNA is not rearranged to produce functioning surface immunoglobulin and T cell receptors. The immunocompromised hosts may also be a result of a non-functioning thymus, irradiation, so as to destroy stem cells, treatment with stem cell specific cytotoxic agents, cytotoxic agents specific for rapidly dividing cells, anti-asialoglycoprotein GM-1, or the like. At a minimum, usually an immunocompromised xenogeneic host will lack functional B- and T-cells, particularly as a result of a genetic defect in immunoglobulin and/or T-cell receptor gene rearrangements.

The chimeric host has a number of applications based on the presence of viable functioning human lymphoid tissue, normally fetal, in the chimeric host. The presence of antigen-presenting cells and T-lymphocytes provides for the opportunity to immunize with an antigen and for the production of B-lymphocytes having the immunoglobulin locus rearranged to produce immunoglobulins having specificity for a predetermined antigenic epitope, or a plurality of epitopes of the same or different antigens. The presence of the cells of the lymphoid lineage, particularly in conjunction with cells of the myelomonocytic lineage, allows for the evaluation of compounds and methodologies on the modulation of the immune response, up or down regulating the production of cells involved with the immune response. Drugs, combinations of drugs, and treatment modalities may be evaluated as to their effect on the expansion and/or inhibition of the proliferation of cells involved with the immune response.

Various sites may be selected for the introduction of the human tissue, where the sites are downstream from a convenient site in the blood or lymphatic system for introduction of the immunogen. In addition, the sites should provide for vascularization as well as lymphatic vessel connection. Sites which have found application include the popliteal fossa, kidney capsule, cervical region, particularly the outer region, peritoneal cavity, and the like. The popliteal fossa is convenient in that the immunogen may be introduced in the foot pad, which will be drained by a lymph node introduced into the popliteal fossa. Similarly, the cervical region is convenient since the immunogen may be injected into the ear. In both of these regions the lymph node becomes connected to the lymphatic system.

Normally, the tissue which is introduced into the host will be allowed to grow and vascularize and have lymphatic vessels connected before immunization. Generally, at least one week will transpire, preferably at least about two weeks, and usually immunization will occur within twenty weeks of transplantation, more usually within two to ten weeks of transplantation, the period being selected to ensure that the tissue is viable prior to harvesting and fusion. Immunizations may be repeated at one to six week intervals, as long as the lymph node remains populated with the appropriate antigen presenting cells and lymphocytes.

The subject transformed host may be used for the production of xenogeneic, normally human, monoclonal antibodies. The subject methodology may be used with any compound having an epitope of interest, including epitopes common to humans. Since there is no concern about the effect of producing antibodies specific to a human protein in the subject chimeric host, one can develop antibodies to native human proteins. Immunogens of interest may be both haptens and antigens, where the haptens are modified to provide for an immune response. Compounds of interest may include small synthetic organic molecules, generally of less than about 5 kD (kilodaltons), usually less than about 2 kD, polypeptides and proteins, lipids, saccharides and combinations thereof. The compounds may be synthetic or naturally occurring, including drugs, hormones, cytokines, surface membrane proteins, enzymes, saccharides, e.g., sugars of proteoglycans and glycoproteins, toxins, envelope proteins, capsid proteins, cytoplasmic proteins, outer membrane proteins, and the like. The immunogen may be combined with a wide variety of adjuvants, such as complete Freund's adjuvant, specol, pristane, B. pertussis or its toxin, muramyl peptides, etc. Usually the injection volume will vary widely depending upon the size of the animal, usually varying from about 10 μl to 5 ml, comprising from about 10 ng to 5 mg of the immunogen, where the amount will vary with the size of the host. The adjuvant would be used in conventional amounts in accordance with the nature of the adjuvant.

Administration will normally be by injection, which will usually be subcutaneous, intramuscular, intraperitoneal or intravascular, where the injection is upstream from the site of the human lymphoid tissue. One or more booster injections may be made, usually within 1 to 6, more usually 2 to 4 weeks after the previous injection, where a booster injection may have the same composition or different composition from the prior injection, by changing the concentration, adjuvant, or the like. In conjunction with administration of the immunogen, IL-6 or other cytokines may be administered, generally to provide a concentration in the bloodstream in the range of about 0.5–20 μg/ml.

Transplanted hosts which are selected are desirably those hosts which demonstrate a significant presence of human immunoglobulin in their peripheral blood, generally having at least about 10 ng/ml of human IgG and/or IgM, preferably at least about 1 μg/ml. Also, the graft should be observed for cellularity and the presence of cells demonstrating surface immunoglobulin.

After the immunization is complete, the tissue may be harvested and the B-lymphocytes immortalized and/or cloned as appropriate. Various fusion partners are available, which are capable of immortalizing human B-lymphocytes. See for example, Kan-Mitchell et al., J. Clin. Lab. Anal. (1989) 3:41–9. The methods employed for the fusion are to combine the B-lymphocytes with the fusion partner in the presence of a fusogen, usually a non-ionic detergent, for sufficient time for fusion to occur, followed by selection of the resulting hybridomas in accordance with the nature of the marker(s) present in the fusion partner. The cells may then be subjected to limiting dilution to provide for clones free of contaminating cells, so as to result in a homogeneous antibody composition. The hybridomas may then be introduced into host animals, e.g., mice or rats, to produce ascites fluid or mechanically expanded, using spinner flasks, roller bottles, etc. The host will be immunocompromised, so as to be able to accept the neoplastic graft.

The resulting antibodies may be used in a variety of ways, both diagnostic and therapeutic. However, since other antibodies which are normally more easily obtained, such as non-human antibodies can be used in in vitro diagnostics, for the most; part the subject antibodies will be used for in vivo diagnostic and therapeutic use in humans. Thus, the subject antibodies may be used in the treatment of septicemia, for ablation of particular T-lymphocyte receptors, for neutralizing viruses or other pathogens, for in vivo diagnosis, for targeted toxicity against neoplastic cells or precursors to such cells, for passive immunization, in conjunction with transplantation, and the like. The subject antibodies may be modified by radiolabeling, conjugation to other compounds, such as biotin, avidin, enzymes, cytotoxic agents, e.g., ricin, diphtheria toxin, abrin, etc., fluorochromes, particles, e.g., magnetic, and the like.

The subject chimeric hosts may also be used in the production of human T-lymphocytes specific for a particular target cell or a particular immunodominant sequence. These T-lymphocytes may be CD4 helper cells, CD8 suppressor cells, natural killer cells, cytotoxic T-lymphocytes, antibody dependent cytotoxic cells, tumor infiltrating lymphocytes ("TILs"), lymphocyte activated killer cells ("LAKs"), etc. The same system that is employed for the production of B-lymphocytes specific for a predetermined antigen may be employed for the production of CD4 helper cells specific for an immunodominant sequence which binds the target major histocompatibility complex to which the T-lymphocyte is restricted. Also, for the other types of T-lymphocytes, by providing for the appropriate stimulus, one may produce TILs, using neoplastic tissue in conjunction with the lymphoid tissue; for other types of T-lymphocytes, using various cytokines and/or growth factors in conjunction with a stimulus, e.g., microorganism, and the like.

The lymphoid tissue may also be used in the studies of vaccines and drugs, as to efficacy in producing an immune response and as to the effect of the drug on the immune system. For a vaccine, lymphoid tissue, such as lymph node, may be used in substantially the same manner as was described for the production of monoclonal antibodies. By providing a base line for response with a number of different vaccines one can compare vaccines as to their response in producing a primary and secondary immune response. In addition, one can immortalize the activated B-lymphocytes and screen the antibodies for their protective effect against the pathogen.

In addition, one can use the lymphoid tissue to determine the effect of drugs on the immune system. One can detect the effect of drugs, including known, modified or to be discovered cytokines, on the viability of human hematopoietic cells in various tissues, the effect of the drugs upon stimulation by immunogens and/or cytokines and the like. By introducing bone comprising bone marrow in the immunocompromised host, and determining the relative population of the cells in the bone marrow and the change in the population in the presence and the absence of a therapeutic dosage of the drug, one can obtain an indication of the effect of the drug on the hematopoietic cells in the bone marrow. By stimulating the lymphoid tissue with an immunogen in the presence and absence of the drug and evaluating the immune response, one can measure the effect of the drug on the immune response, i.e. humoral or cellular. To measure the effect, one could determine the number of cells which have been activated (e.g., to produce sIg), by preparing tissue slices, labeling the sIg for the immunogen and counting the number of cells which are specifically labeled.

The chimeric host may also be used for evaluating the cytotoxicity of various drugs toward the foreign tissue, for example, for screening for investigative new drug applications. In addition, the chimeric host may be used to evaluate the drugs as to their efficacy, safety and bioavailability.

Paradigmatic of pathogens is the determination of efficacy for drugs for the treatment of viruses. Exemplary of viruses is HIV, the agent which causes AIDS.

Various isolates of HIV may be employed for studying the efficacy of drugs. Normally, isolates which have been extensively passaged in tissue culture (in vitro) and transfection into human T-cells should be avoided. Therefore, the virus which should be employed may be obtained form fresh blood, cerebral spinal fluid, brain or other tissue infected with the virus, may be cloned and then frozen down to be used, or the like, usually having been passaged fewer than about ten times, preferably fewer than about five times. Administration is preferably intravascularly, but may be intraorgan, particularly with the thymus, intraperitoneally, subcutaneously or the like. Generally, for HIV, the dosage introduced intravenously will generally be the equivalent of at least about 15 ng p24, more usually at least about 25 ng p24, and preferably at least about 30 ng p24 (30,000–3,000,000 $TCID_{50}$) (Doses introduced intra-organ will be correspondingly lower). Infection should be performed within about four weeks of implantation of the organ.

The presence or absence of viremia may be determined in a variety of ways. The polymerase chain reaction ("PCR") may be used for qualitative or semi-quantitative determination of the level of viremia. In this assay, venous blood is obtained, prepared for virus isolation using standard techniques, and assayed for viral RNA. Alternatively, the blood may be assayed for p24 or other viral protein, using ELISA or other assay. Commercial assays exist for detection of p24.

For quantitative determination, blood samples are obtained, the virus obtained by differential centrifugation in a PBS-EDTA buffer, dispersed in Tris-saline-EDTA buffer, heated to 80°–90° C., protein enzymatically digested, the sample washed in Tris buffer, taken up in Tris-EDTA, heated at 50°–70° C., cooled and reversed transcribed. In this manner the RNA and cDNA is obtained substantially free of cells and cell components. The RNA is reverse transcribed, amplified at about 30 cycles with PCR and detected using a chemiluminescent labeled probe, e.g., acridinium.

For other pathogens, tissue capable of being infected is transplanted into an appropriate site in the mouse and allowed to form whatever connections are appropriate, such as vascularization or connection with lymphatics, or other organs or vessels in the host. Once the tissue(s) and, as appropriate, circulating cells have become established, the tissue may then be subjected to the agent for investigation or product production, depending upon the nature of the tissue (s), the agent, the purpose for which the agent is used, convenience, and the like. The agent may be introduced by injection, intravascularly, intraperitoneally, directly into the tissue, topically, intranasally by an aerosol, or the like.

Depending upon the particular agent and investigation, various bioassays may be employed. Where one is interested in replication, such as in viremia, one may detect various proteins produced by the virus or nucleic acid associated with the virus, at the tissue site, in the peripheral blood, or other site of interest. Various assays exist for identifying specific DNA, virus particles, specific proteins, or the like, where these assays find extensive exemplification in the literature and need not be detailed here.

The following examples are offered by way of illustration and not by way of limitation.

EXPERIMENTAL

Methods

1. Mice.

CB-17 scid/scid mice were obtained from Dr. Leonard D. Shultz of The Jackson Laboratory, Bar Harbor, ME. The mice are housed in standard isolator cages within a routine animal holding facility. Under these conditions, they have a life span that is considerably shorter than that of other inbred immunocompetent strains (e.g., 1–2 years vs. 3–4 years). The cause of death is normally related to opportunistic infection (most often by *Pneumocystis carinii*). Protocols to prevent such infections by administering prophylactic antibiotics (trimethoprim/sulfamethoxasole) to the mice are being employed (see above) using as guidelines protocols developed for the prophylaxis of patients with AIDS or ARC. In all other respects (e.g., bedding, food, daily light cycles, etc.), the mice are handled as per routine animal holding facility protocols.

2. Collection and preparation of human fetal tissues.

The information that is known about the patient includes the approximate (or where known, the actual) gestational age of the fetus and the given reason for the abortion; in the latter case, also known are the details of any genetic or morphologic anomaly discovered by amniotic fluid analysis and/or ultrasonography (e.g., chromosomal defects, anencephaly, hydrops, etc.). In initial experiments, tissue from fetuses that are apparently normal were used; in later experiments, specifically constructed situations were created in which tissues from fetuses with genetic anomalies were tested.

The tissues are obtained directly in the operating room as fetal parts after elective or medically-indicated abortion (with gestational ages ranging from 7–22 weeks). Without maintaining strict sterility, these parts are taken immediately to a gross dissection room. The desired tissues are identified, dissected out, placed into RPMI 1640 medium with 10% fetal calf serum, and transported directly to another lab. In those situations in which "whole organ" transplants (i.e., tissue inclusive of both the stromal elements and of the hematopoietic elements therein) are being performed, the relevant organs are cut into sections that are approximately 1 mm by 4 mm. (A piece of tissue of this size fits easily into the 19-gauge trocar that is used for implantation.) In those situations in which dispersed cells are to be injected, the relevant organs are teased apart to yield viable cells in suspension. In the case of fetal liver, the suspension cells are enriched for hematopoietic precursors by ficoll-hypaque density gradient centrifugation; the interface layer containing the desired cells is then washed 3×, counted, and brought to approximately $10^8$ cells/ml. For subfractionation of hematopoietic precursor cells, fetal liver cells isolated on ficoll-hypaque gradients are subsequently stained with monoclonal antibodies against relevant cell surface markers and isolated by techniques including negative selection with magnetic beads and positive selection on the fluorescence activated cell sorter (FACS).

To mark the genetic origin of the donor fetal tissue, HLA histotyping is performed on fetal thymocytes using monoclonal antibodies (see below) that recognize common HLA alleles. In this manner, prior to implantation, a histotyped "fingerprint" is obtained by which all subsequent progeny of the introduced stem cells may be specifically followed in the SCID-hu mouse.

Tissue is normally introduced in as fresh a state as possible. Therefore, the tissue collection, preparation, histotyping, and implantation are done all on the same day. Frozen tissue, however, appears to work well in the case of fetal liver cells and fetal thymus tissue. Therefore, aliquots of remaining tissue from each specimen are frozen down at the end of the day 10%DMSO/50%FCS using standard procedures and then catalogued in a liquid nitrogen storage freezer.

3. Transplantation of human tissue into SCID mice.

Mice have generally been used at 4–8 weeks of age, either without pretreatment or after pretreatment with either (a) anti-asialoglycoprotein GM1 or (b) fractionated courses of irradiation (175 rads weekly×4 weeks). The latter two pretreatment regimens have been designed to test the possibility that removal of endogenous natural killer cell activity in the SCID may permit better constitution with xenogeneic tissue.

Tissue has been introduced by a number of routes: intravenously, beneath the kidney capsule, intrasplenically, intraperitoneally or subcutaneously. In the latter three cases, the mice are first anesthetized with halothane. A 1 cm incision is made to expose either the kidney or the spleen and a 19 g trocar is used to introduce human tissue beneath the capsule of either organ. Thereafter, the incision is approximated with surgical sutures. For intravenous injections, a 30 g needle is used to introduce suspension cells into the retro-orbital venous plexus. Of these routes, implantation of tissue into the left kidney capsule affords several distinct advantages: first, it is easily accessible; secondly, the kidney may be exposed repeatedly to observe the growth of the transplanted tissue and to remove biopsy specimens from it for histologic analysis.

4. Analysis of SCID-hu mice.

A. Immunophenotyping.

A number of monoclonal antibodies against various cell surface markers of human lymphocytes have been prepared for the analysis of cells found within SCID-hu mice. These include markers of mature human peripheral blood T-cells (OKT4, OKT8, OKT3, OKT11), markers of human peripheral blood B-cells (CD19, CD20, anti-IgM, anti-IgG, anti-light chain), and markers of the human HLA complex (including both polymorphic and monomorphic determinants of Class I antigens). These murine antibodies have been used in immunofluorescence assays, either as primary antibodies that are secondarily reacted with fluoresceinated (FITC) anti-mouse antibody, or as biotinylated antibodies that are secondarily reacted with avidin-FITC. In some instances, antibodies that are directly fluoresceinated or coupled with phycobiliproteins have also been used. After transplantation, mice are bled weekly by tail vein incision or retroorbital bleed; approximately 100 µl of whole blood is obtained (usually containing $1–2×10^5$ cells). Nucleated cells are enriched by precipitation of red blood cells with dextran sulfate, or by lysis of red blood cells with hypotonic shock, washed free of platelets, and then stained with the monoclonal antibodies within 96-well microtiter plates. After the assay is complete, a visual inspection for positive cells (that is, those with unambiguous surface fluorescence) is made under the immunofluorescence microscope. If human cells represent greater than 1% of the total nucleated cells in the periphery, they may be readily detected by this method and also quantitated with statistical significance with a multiple parameter FACS. Accordingly, if the samples are positive by direct inspection, they are then analyzed by FACS. In this analysis, the cells are fixed first with 1% formalin and then incubated for 10 min with 1 µg/ml propidium iodide (PI) (which is taken up by nucleated cells). In subsequent FACS analyses, cells are first gated for PI (that is, they are nucleated) and then assessed for staining with FITC. In this manner, the percentage of FITC-positive cells as a function of total nucleated cells may be readily obtained.

B. Histology.

At various times post-transplantation, tissues are taken either by biopsy (of, e.g., the tissue growing beneath the left renal capsule) or by autopsy and frozen on O.C.T. for thin-section. Thereafter, sections are stained with the above monoclonal antibodies and counterstained with a secondary alkaline phosphatase-labelled secondary antibody. The presence of cells positive for the marker is then detected with the alkaline phosphatase reaction product of diaminobenzidine and visualized under light microscopy.

C. DNA analysis.

Cells taken by tail vein bleed or by resuspension of organ systems after biopsy or autopsy are treated by standard methods for the extraction of total cellular DNA. Total cellular DNA derived from SCID-hu mice has been analyzed using various probes and assay systems and compared in parallel to DNA obtained from untreated SCID mice or from normal human controls. The probes include the following: 1) Alu repeat (BLUR 8), a repetitive sequence of DNA found in the human genome but not homologous enough to murine sequences to cross-hybridize under the conditions used in these experiments, 2) human T-cell receptor (B chain) probes, 3) human Ig constant region probes, 4) human MHC Class I and Class II probes. For use in dot blots and in Southerns (run under standard conditions), these probes are first labelled with $^{32}P$ by the hexamer-labelling technique. Rearrangements in the T- and/or B-cell receptor genes are sought by restriction endonuclease digestion of total cellular DNA, using known restriction maps and standard conditions. For polymerase chain reactions, using the thermostabile Taq 1 polymerase, a number of oligonucleotides have been constructed and/or obtained, including those to generate copies of the Alu repeat as well as of the Class I and Class II monomorphic sequences.

D. Karyotype analysis.

For karyotype analysis, cells taken by tail bleed have been put into culture with phytohemagglutinin to induce proliferation of human cells. At 48 hours, metaphase arrest is induced by the addition of colchicine and chromosomes prepared for analysis by light microscopy.

Results

1. Human fetal thymus grows in SCID mice.

The growth of human fetal thymus has been observed in most (>80%) SCID mice that have been transplanted with human fetal thymus (including >300 mice in successive experiments at various times over about an 18-month period). In those cases where tissue growth is not observed, problems related to implantation technique are likely to be the cause. The gross architecture is observed by re-opening the flank incision initially made to implant the thymic specimens and exposing the kidney. By 4–8 weeks post-implantation, marked increase in size is almost invariably evident (in very approximate terms ranging from a two-fold to a 20–30 fold increase). In several cases, fragments of human fetal thymus implanted into one mouse have been removed and transferred to a second, previously untreated mouse. In these cases as well, dramatic growth of thymic tissue has been subsequently observed. The thymus is similar to that of normal human fetal thymus in both color and in consistency. A well-defined vascular system may be observed with low-power magnification. When biopsy specimens are prepared for tissue section and stained with monoclonal antibodies against antigens present on human or murine cells, it is found that the cellular contents of the implanted thymus are mostly human (see below) and that the microscopic anatomy of the tissue has been generally conserved. Thus, well-defined medullary and cortical compartments are present, with characteristic staining of epithelial components with the antibodies MD1 and CDR2, respectively. Dendritic-like cells positive for human Class II determinants are found in the medulla and, to a lesser degree, in the cortex. Thymocytes which stain for the human T-cell markers CD3, CD4, CD8, and CD2 are also present. When analyzed by dual-laser FACS, the percentage of cells that are double-positive for CD4 and CD8, single-positive for CD4 or CD8, or double-negative for both markers is similar to that found in a normal, age-matched fetal thymus. The above findings have been made with mice that have received thymic tissue from human fetuses aged 9–22 gestational weeks.

The only difference noted to date between the SCID-hu thymus implant and a normal human fetal thymus is the presence, in the former but not in the latter, of dendritic-like cells in the cortex and (to a lesser degree) in the medulla which express murine Class II determinants. These cells are likely derived from murine, bone-marrow precursors which migrate into the vascularized SCID-hu thymus implant.

A number of important conclusions may be drawn from the above observations. First, human fetal thymus tissue is not rejected by the SCID mouse. Indeed, it is richly vascularized and grows instead. Secondly, by gross morphology and microscopic anatomy, the implanted human thymic tissue bears close resemblance to its normal human counterpart. Thus, the organ appears to maintain intrinsic properties for spatially correct regeneration.

Also, the number of and relative subset distribution of thymocytes appears to be normal. Finally, murine dendritic cells bearing murine Class II determinants are found in the SCID-hu thymus. These cells may be involved in "teaching" the developing human thymocytes to be tolerant of (and possibly MHC-restricted to) murine MHC antigens. Thereby, graft-versus-host disease may be averted.

2. Phenotypically mature human T-cells are found in the peripheral circulation of SCID-hu mice.

This phenomenon has been observed in >300 sets of experiments. By FACS analysis using monoclonal antibodies against human T-cell markers, it is predictably time-dependent, occurring 4–12 weeks after intravenous introduction of human fetal liver cells into a SCID mouse previously (or simultaneously) implanted with human fetal thymus.

Specifically, sets of mice received human fetal thymus implants. These sets were subdivided into groups: some received $10^7$ fetal liver cells (FLC) intravenously at the same time, some received $10^7$ fetal liver cells intrathymically two weeks later, some received no fetal liver cells at all. At three weeks, the peripheral blood of each was tested for the presence of cells staining for the human T-cell markers CD3, CD4, CD8, CD2; all were negative. By 4–12 weeks, however, such cells were visible on FACS (constituting 0.2–40% of the total mononucleated cell population). The ratio of $CD4^+$ to $CD8^+$ human T-cells in SCID-hu peripheral circulation during this time was between 3–4 (mean 3.5, n=85, S.D.=0.86), well within the normal range. Tested again between 12–15 weeks post-FLC transplantation, cells bearing these markers were no longer present. This general pattern was true irrespective of the route by which FLC cells were initially administered.

From this analysis it appears to take 4 weeks for significant numbers of cells bearing markers of human T-cells to appear in the peripheral blood of SCID-hu mice. Before that time, they are not present; after 12 weeks, they disappear. A corollary is that immunophenotyping is probably legitimate; that is, the antibodies that were used are only reactive in a time-dependent manner and appear not to bind indiscriminately to murine cells. Of interest, the transient wave of human T-cells in the periphery may occasionally be observed whether or not fetal liver cells are given. This appears to mean that cells that are resident within the fetal thymus, at the time that it is implanted, are also able to exit the thymus and to enter the peripheral circulation.

After it had been determined that peripheral blood cells bearing human markers were absent from the SCID-hu animals, all were once again reconstituted with FLC; notably, all of these animals retained the original human fetal thymus implants. In this second round of reconstitution, the animals were once again subdivided into groups: some received graded doses of FLC cells intravenously (ranging from $5 \times 10^6$ to $5 \times 10^7$); other received fragments of whole fetal liver, given both subcutaneously and intrasplenically. Analysis of peripheral blood 3 weeks later revealed the complete absence of cells bearing human markers. By 6 weeks, on the other hand, animals once again showed the presence of significant numbers of cells bearing the human markers CD3, CD4, CD8 and CD2 (approximately 4–30% of total mononuclear cells); notably 3–15% of these cells expressed the CD4 marker. When two mice were subjected to autopsy one week later (week 7), both showed cells in the periphery that stained either with OKT4 (a marker of the T helper cell lineage) or with OKT8 (a marker of the T cytotoxic/suppressor cell lineage(s)); the ratio of the two respective subpopulations was 2.3:1, well within the range of the normal ratio found in human peripheral blood itself. To ascertain whether these cells might actually home to the murine spleen, thymus, or lymph node, FACS analysis was also performed on cells obtained from these organs. In these cases, no cells bearing the human T-cell markers were observed. In subsequent FACS analyses of peripheral blood, all but one set of mice were observed to once again lose the peripheral population of human T-cells.

When SCID mice are implanted with whole fetal liver fragments and fetal thymus, and then given an intravenous injection of fetal liver cells, the same observations are made with a critical difference. Instead of lasting only 12 weeks, the human T-cells in the peripheral circulation are found to last up to 18 months (50% of animals show T-cells between 5 to 11 months). Again, the CD4/CD8 ratio is normal throughout.

This second round of reconstitution prompts a number of important conclusions. First, the phenomenon of a transient wave of human cells in the peripheral blood of SCID-hu mice given FLC intravenously is reproducible. Secondly, since the FLC were given intravenously and since they subsequently showed markers of mature T-cells, it is likely that they actually homed to and through the implanted human fetal thymus. Thirdly, the mature T-cells found in the periphery express a "physiologic" balance of CD4/CD8 subpopulations. Fourthly, it is apparent that these peripheral human T-cells do not actually home to the resident murine organs (spleen, lymph node, thymus). Thus, in ongoing experiments, the human equivalents have been implanted into SCID-hu mice. Finally, the introduction of whole fetal liver is found to generate a prolonged wave of human cells in the periphery. This observation implicates the presence of a self-renewing stem cell population within FLC, which is unable to replicate in the absence of fetal liver stromal cells.

Notwithstanding the apparent specificity of the monoclonal antibodies against human mature T-cell markers (note, even in those mice that showed high percentages of staining cells in the peripheral blood, spleen cell populations analyzed at the same time were negative), it remained a formal possibility that the staining was due to an unforeseen artifact. To control for this possibility, DNA analysis of the cells found in the peripheral blood was performed using a probe specific for human, but not murine, repetitive DNA sequences (the ALU repeat: BLUR-8). By this analysis, it was found that the peripheral blood cells derived from the SCID-hu mouse not only bear the phenotypic markers characteristic of human T-cells, but also contain DNA that strongly hybridizes with the human ALU probe.

When SCID mice are implanted with human fetal thymus and lymph node, and then given an intravenous injection of human fetal liver cells, human IgG may also be detected in the serum. The amount of IgG varies between 5-10% of that found normally. The plasma cells producing the IgG can be localized to the implanted human lymph node. Human IgG production requires at least the introduction of human lymph node into SCID mice.

In a specific experiment SCID mice were maintained in bonneted isolation cages and received TMS in suspension through the drinking water for 3 days of each week (40 mg of trimethoprim and 200 mg of sulfamethoxazole per 5 ml of suspension; 0.125 ml of suspension per 4 ml of drinking water per mouse per day). The drinking water bottle was turned daily while the drug was being administered; standard drinking water was substituted for the remaining 4 days of each week. A 9 g.w. human fetal thymus lobe 0.5 by 0.5 by 2 mm in size and 0.5 by 0.5 by 2 mm segment of a human lymph node were implanted under the left kidney capsule. These organs were obtained from an HLA-A2$^+$, HLA-B7$^-$ donor. Simultaneously, the mouse had received $10^7$ liver cells intravenously; these cells, in contrast, were HLA-A2$^-$, HLA-B7$^+$.

The fetal liver cells were obtained by mincing and cells remaining suspended in RPMI 1640 medium with 10% FCS were separated into mononuclear fraction by ficoll-hypaque centrifugation; the interface cells were then washed 3× in RPMI 1640 with 10% FCS and resuspended at a concentration of $10^8$ cells/ml for intravenous administration.

For implantation of tissue, mice were first anesthetized with halothane. A 1-cm flank incision was made to expose the left kidney. Sutures were placed to approximate successive peritoneal and fascial layers and metal clips were secured over the wound to ensure healing. Suspended fetal liver cells were injected intravenously by a retro-orbital approach with a 30-gauge needle.

Frozen serial fixed sections of the thymus four weeks after implantation were compared to a normal age-matched fetal thymus. The microscopic anatomy was found to be comparable, with the exception of murine Class II-positive cells having a dendritic morphology being present. In particular, all of the thymocytes were HLA-A2$^-$, HLA-B7$^+$; therefore, they were derived from stem cells within the FLC preparation given intravenously.

When peripheral blood from the SCID-hu mice were analyzed, human T-cells with a CD4/CD8 ratio of 3.5 were found between weeks 4–12. These cells expressed the antigen HLA-B7, but not HLA-A2; therefore, they were fully differentiated cells from the original FLC source, having been processed first through the HLA-A2$^+$, HLA-B7$^-$ thymus.

Finally, when serum specimens from the SCID-hu mice were analyzed, they were found to contain human IgG at levels of 1–10 mg/ml. Human lymph node biopsies showed the presence of human IgG-containing plasma cells by immunohistochemical stain.

3. Infection with Infectious Agent—HIV.

In another study, the ability to cause lymphotropic infection with a human-specific pathogen was studied. Particularly, an HIV-1 isolate was employed for infection, where the isolate was found to be infectious in vivo but not in vitro.

A molecularly-cloned isolate of HIV-1 was used. Derived from the cell-free cerebrospinal fluid of a patient with subacute encephalopathy and Kaposi's sarcoma, HIV-1$_{JR-CSF}$ was propagated first in short-term culture with phytohemagglutinin-stimulated human peripheral blood lymphocytes in vitro and then molecularly cloned. This isolate has found to be infectious for mitogen-stimulated human T-cell blasts and for glial cell explants, but not for primary monocyte/macrophage cultures. It has not been passaged, and does not grow, in continuous human T or monocyte/macrophage cell lines. Such tropism marks a potentially important difference between it and other isolates which have been molecularly cloned and adapted to growth in Vitro (e.g., HXB2, HTLV-III$_B$, ARV, and LAV).

A flank incision was made to expose the growing human thymus or lymph node implant of anesthetized SCID-hu mice. Graded doses of HIV-1$_{JR-CSF}$ were introduced by direct intra-thymic or intra-nodal inoculation. The mice were then maintained within micro-isolator cages, inside a glove box. At varying time points, biopsy specimens of the infected lymphoid organs were prepared, fixed in 4% paraformaldehyde, and assayed for signs of acute infection.

Infection of SCID-hu mice with HIV-1$_{JR-CSF}$ resulted in easily detectable signs of viral replication. The most directly informative assay has been in situ hybridization of infected tissue sections with the RNA probe pG4. This probe hybridizes to the 3' end of the genomic HIV-1 transcript; accordingly, all viral messages are detected without discrimination. Under the conditions of the assay, viral DNA is not detected. The results indicate that infection of the human thymus and lymph node implants is time-dependent. At one week after direct intra-thymic inoculation (of 400–4000 infectious units), no cells in the section were seen to hybridize with the pG4 probe. At 2, 4, and 8 weeks, progressively increasing number of cells were found to hybridize (see Table 4). This suggests that ongoing rounds of infection occurred in vivo. The infected cells were scattered throughout the cortex and medulla of the injected human thymus and diffusely across the injected human lymph node. Discrete foci of infection, involving more than one contiguous cell, were only rarely observed. Possibly, within a given tissue implant, contiguous cells may be either resistant to infection or infected at an undetectable level. Alternatively, infected cells may disseminate from another focus, not included in the section (e.g., from migrating progenitor cells, infected elsewhere).

TABLE 4

QUANTITATION OF INFECTION BY HIV-1 IN THE SCID-HU THYMUS

| | Week Post-Infection | | | |
|---|---|---|---|---|
| | 1 | 2 | 4 | 8 |
| Medulla | | | | |
| ISH+ | 1 | 30 | 50 | 116 |
| IH+ | ND | 4 | 30 | 31 |
| % +/+ | — | 10 | 60 | 29 |
| Cortex | | | | |
| ISH+ | 1 | 12 | 6 | 24 |
| IH+ | ND | 0 | 2.5 | 7 |
| % +/+ | — | 0 | 45 | 31 |

ISH — in situ hybridization
IH — immunohistochemistry - viral protein (GB)
Results expressed are the number of infected cells, cells detected by ISH or IH, in 10 independent high power (200X) fields. Read by two observers.

The events described are specific for HIV-1 infection. Prior heat-inactivation of virus (80° C., 1 hr) destroyed infectivity. No cells in infected tissue were found to hybridize with pG4 RNA probes in the "sense" orientation. No cells in uninfected tissues were found to hybridize to pG4 probes in either orientation. Finally, the infection is not only time-dependent but also dose-dependent. Thus, a $10^{-1}$ dilution of HIV-$_{JR-CSF}$ was found to be infectious, but dilutions of $10^{-3}$–$10^{-5}$ were not. Using estimates of viral titers determined by in Vitro assays, the $10^{-1}$ concentration corresponds to 400–4000 infectious units.

The above analysis was expanded by applying immunohistochemical stains to the tissue sections, prior to in situ hybridization. In this manner, the presence of viral protein could be detected in cells making viral RNA transcripts; in addition, the cell surface phenotype of infected cells could be determined. In this case, a polyclonal antiserum (GB) reactive against gag, pol, and env epitopes was used to analyze sections of human thymus, two weeks after infection with HIV-1$_{JR-CSF}$. More cells were found to be infected in the medulla than in the cortex, even though there was an abundant representation of CD4+ thymocytes in each compartment. A similar situation was found at weeks 4 and 8 post-infection, throughout multiple planes of observation. Thus, within any given section at any given time, 70–90% of the infected cells were medullary in location. Rarely, infected multinucleated cells, perhaps representing syncytia, were seen.

In both the medulla and the cortex of the thymus, as well as in the lymph node, two distinct modes of viral replication were apparent by combination immunohistochemistry and in situ hybridization. In one mode, cells were found to make detectable amounts of viral protein and RNA; in another, only viral RNA transcripts were found. The latter population represents the majority of the total infected cells in each compartment (Table 4). The basis for this observation is not clear. An artifact related to the procedure itself appears unlikely, cells expressing each mode of replication are randomly dispersed and frequently adjacent. Rather, those cells which are not stained with the antiserum GB may be making viral protein at levels below the level of sensitivity for detection; alternatively, they may be making different vital proteins (e.g., with epitopes not detected by the various antibodies in the serum).

In either case, disparate patterns of transcriptional and/or translational control post-infection must be invoked. Since the results are obtained from infection with a molecular clone of HIV-1, it is likely that unique cellular environments dictate the differences in control. These various environments may be inclusive of distinct cell lineages and of successive steps of activation or differentiation within given lineages. Complex patterns of this sort have been documented in vivo after infection with other lentiviruses (e.g., visna, canine arthritis-encephalitis virus). Their existence is consistent with recent experiments on HIV-1 in Vitro. The regulatory mechanisms by which they occur may now be explored with HIV-1 in vivo, within the SCID-hu mouse.

It is important to note that the SCID-hu mouse has proved permissive for infection by isolates of HIV from patients or cloned HIV isolates, which were not adapted to tissue culture conditions. Contrastingly, 0 of 5 tissue culture adapted isolates were not infectious in the SCID-hu mouse.

4. Transplantation of lymph node into mammary fat pads.

Recipients are 6–8 weeks of age. All transplantations are performed under sterile conditions in a vertical, sterile, air-flow hood. After receiving transplants, the mice are housed in microisolator cages (Lab Products).

The human mesenteric lymph node with the peritoneal fascia of the mesentery (containing efferent and afferent blood vessel and lymphatics) was obtained as approximately a 2 mm elliptical tissue slice. The prepared SCID mice were removed from the microisolator, in a vertical laminar sterile air-flow hood, anesthetized with pentobarbital sodium (0.01 ml/g body weight; solution of 6.7 mg pentobarbital sodium/ ml in 9% ethanol) and taped on sterile operating boards. By an aseptic technique, the number four mammary fat pads were exposed through a midline ventral incision. Sharpened watchmakers forceps were used to create a defect in the mammary fat pad through which the mesenteric lymph nodes were introduced. The ventral skin incision was then closed with 7.5 mm wound clips.

In SCID mice implanted as described above 100% of the mice were found to result in the growth of the lymph node. Anastomoses were found to occur between the blood vessels of the transplant and the host blood vessels. Prompt vascularization was observed, as well as generation of human primary follicles over a period of 3–6 weeks.

The central artery in the human lymphoid follicle was shown to be of murine origin in a microscopic section. Except for chimeric vascularization and encapsulation by murine fibrous tissue, the architecture of the node was found to be that of a normal human lymph node by immunohistochemistry in histologic sections.

The nodes appeared to grow steadily within the SCID-hu mouse for a period of time ranging from 2–10 weeks.

5. Quantitative PCR for detecting viremia in blood samples from HIV infected SCID-hu mice.

Blood samples (0.2–0.3 ml) plus 0.1 ml PBS-EDTA were spun 7,000 rpm for 5 min, the plasma separated from the pellet and spun 10,000 rpm for 5 min to remove debris. The supernatant is spun at 15,000 rpm for 2 h to provide a pellet comprising the virus.

The pellet is dispersed in NAT buffer (0.5M NaCl, 1% SDS, 10 mM Tris, pH 7.5, 1 mM EDTA) (800µ), heated at 85° C. for 20 min, cooled 20 µl of 200 µg/ml proteinase K and 2 μl RNasin (Promega) added to each sample, vortexed and then incubated at 37° C. for 1 h. Using a long 26 ga needle a tiny quantity of oligo-dT cellulos (NEB) is added to each sample and the mixture tumbled at 37° C.

The samples are microfuged at 10 Krpm for a few minutes, the supernatant discarded and 500 μl wash buffer (0.5M NaCl, 0.2% SDS, 10 mM Tris, pH 7.5, mM EDTA and 1 mM PMSF) added. Microfuging, addition of wash buffer and discarding supernatant are repeated, followed by addition of 500 μl final buffer (0.5M NaCl, 10 mM Tris, pH 7.5, 1 mM EDTA), the mixture vortexed, microfuged at 10 Krpm for a few min, supernatant discarded and 50 μl TE (10 mM Tris pH 7.5, 1 mM EDTA) added. After microfuging at 10 Krpm for a few min, supernatant is collected, pellet treated with TE a second time as before and supernatants combined. The solution is heated at 65° C. for 5 min, chilled on ice and the RNA transcribed using 10 μl 5xRT (reverse transcriptase) buffer, 10 μl dNTPs, 1 μl of 1 μg/ml Return Primer (ex 661, SK 39) and 2 μl MMLV-RT (BRL) following instructions of the vendor.

The PCR amplification is then performed in accordance with the conditions suggested by the vendor (PE-Cetus), with the primer concentration being 1 μl of 100 ng/ml for each primer in ~100 μl of mixture. Thirty cycles are used, showing linear correlation for 10–10,000 molecules.

The detection system used for measurement is provided by Gen-probe, Inc., San Diego, California, using acridinium label and measuring by chemiluminescence.

PCR products are first hybridized with oligonucleotide probes that have been coupled with an acridinium ester. After hybridization, acridinium attached to unbound probe is selectively hydrolyzed; acridinium attached to a bound probe is measured by chemiluminescence. The relative light unit (RLU) reflects the total copy number of amplified fragments in the sample. To establish a standard titration curve, the RNA samples used in the above isotopic assay were amplified for 25 cycles by PCR and then measured with the non-isotopic assay. The curve is linear over four log orders of virus dilution, ranging from 600–600,000 $TCID_{50}$. To shift the curve towards the right (to read lover amounts of virus), PCR was continued for 30, instead of 25 cycles. The resulting curve is still linear over log orders, but now ranges between 60–60,000 $TCID_{50}$. Given that the level of viremia in SCID-hu mice appears to range between 10–2,000 $TCID_{50}$, these are the conditions that are being used.

The PCR products were run on 1% agarose gels, transferred to nitrocellulose and hybridized with $^{32}$P-kinased detection probes; the autoradiogram was then scanned on a densicytometer. The standard curve was linear over four log orders of virus dilution. $TCID_{50}$ values for this curve were calculated on the basis that, for HIV strain JR-CSF, 1pg p24=4 $TCID_{50}$. This standard curve has been reproduced in several experiments.

SCID-hu lymph node mice, having the lymph node in the mammary fat pad, were infected with various isolates of HIV including JR-CSF, JR-CSF-X, JR-FL, SM, HTLV-IIIB, HXV-2 and 2NEF+ mutants derived from it. The following are the results.

TABLE 5A

| VIRUS | TCID(50) (INPUT) | PLASMA RNA PCR (6 WEEKS) Viremic Animals/ Animals Tested |
| --- | --- | --- |
| JR-CSF | 120000 | 4/4+ |
| JR-FL | 120000 | 5/5+ |
| SM | 1200000 | 3/5+ |
| IIIB | 1200000 | 0/5+ |
| NONE | 0 | 0/3+ |

TABLE 5B

| VIRUS | TCID(50) (INPUT) | PLASMA RNA PCR (1 AND 2 WEEKS) Viremic Animals/ Animals Tested |
| --- | --- | --- |
| HXB-2 | 12000 | 0/4+ |
| R7/3 | 120000 | 0/4+ |
| HXB2-3gpt | 120 | 0/4+ |
| JR-CSF | 120000 | 3/3+ |

TABLE 5C

| VIRUS | TCID(50) (INPUT) | PLASMA RNA PCR (1 WEEK) | PLASMA RNA PCR (2 WEEKS) Viremic Animals/ Animals Tested |
| --- | --- | --- | --- |
| JR-CSF | 120000 | 3/3+ | 3/3+ |
| JR-FL | 120000 | 5/5+ | 5/5+ |
| JR-CSF-X | 1200 | 0/5+ | 0/5+ |
| SM | 120000 | 8/9+ | 10/10 + |

Greater than 130 plasma samples from various time points after infection of SCID-hu lymph node mice were analyzed for HIV p24 antigen. All were negative until recently when plasma from a few mice contained p24 levels in blood above background. In general, the mice with p24 in their plasma were infected with SM and contained a level of viremia higher than that usually obtained with JR-CSF infection as observed by detectable p24 and quantitative PCR. These data suggest that the experiments are close to the detection limit of viremia by the p24 antigen assay. Attempts to increase the level of viremia by construction of mice with 4 lymph nodes and subsequent IV infection with JR-CSF followed by p24 analysis and quantitative RNA-PCR for viremia, showed negative results for p24 and less than a 4 fold increase in viremia.

Several factors may be interfering with virus isolation. These include (1) factors endogenous to murine serum that are virucidal or virustatic; (2) exogenous factors added during the course of virus isolation which inhibit infectivity; and/or (3) a low absolute virus load in HIV-infected SCID-hu mice. Preliminary experiments indicate that both heparin and EDTA as anti-coagulants do interfere with virus infection at the concentrations used. Rescue of virus by co-culture with human PHA activated T-cells resulted in p24 positive cultures in 11% (8–60) of attempts from plasma and 8% (5–60) from peripheral blood cells after 28 days in culture.

In the study with the lymph node SCID-hu mice, 120,000 $TCID_{50}$ of the virus stock JR-CSF were administered intravenously; after 2 weeks, over 95% of infected animals were viremic. This dose was altered in log orders. After 12,000 $TCID_{50}$, 50% of the animals were viremic after 2 weeks; with 120–1200 $TCID_{50}$, 25% were viremic; with 12 $TCID_{50}$, none were viremic. Parallel DNA PCR analyses of lymph nodes from these animals gave consistent results.

Since lymph node implants maintain their morphology for 4–8 weeks, it was important to establish what effect different time periods after construction of the SCID-hu mice have on infection with HIV. Several groups of mice were infected at various time periods after implantation of lymph node; human lymph node tissues were then biopsied at 2 weeks post-infection for DNA PCR. At 2 and 4 weeks post-construction, infection with HIV resulting in viremia is greater than 95% of animals at 2 weeks; if SCID-hu mice are infected at a time period over 4 weeks, susceptibility to infection progressively declines.

In light of the above data, the standard protocol for intravenous infection of SCID-hu mice involves implantation with fetal lymph node in the fourth mammary fat pad. Within 4 weeks, 120,000 $TCID_{50}$ of a standard stock of JR-CSF (corresponding to 30 ng of p24 ELISA) are inoculated intravenously. Two weeks later, venous blood is obtained, prepared for virus isolation, and assayed by RNA PCR.

The effect of drugs on the course of viremia after HIV infection was then studied.

AZT (200 mg/kg/day) blocks infection in the SCID-hu thymus when administered 1 day prior to infection and maintained for 2 weeks thereafter in the drinking water. At 200 mg/kg/day, 100% of lymph node SCID-hu mice infected by the intravenous route were protected. In contrast to intrathymic infection, the lymph node animals remained aviremic 4 weeks after the cessation of AZT therapy.

Dose response experiments for AZT were conducted. The "protective dose 50" of AZT (the dose of which 50% of animals were viremic when treated prophylactically) was 60 mg/kg (days to be understood, beginning 1 day before infection and continuing for 2 weeks). In comparison, the lowest dose now found effective in man is 5–10 mg/kg (300–600 mg per day/60 kg patient). In converting dosage given to mice to those that are equivalent in man, the murine dose (mg/kg) is normally divided by a factor of 12 to account for differences in metabolic rates. The dose range of AZT as determined by the above study for complete protection is similar to the dose rate presently used in the treatment of AIDS patients.

ddI was administered in varying dosages to lymph node SCID-hu mice by intraperitoneal injection, twice daily for 1 day before infection and 2 days after infection, then once daily for the next 12 days. At 200 mg/kg/day, viremia was completely suppressed. Decreasing dosage generated a curve, which indicates that the "protective dose 50" is 13 mg/kg/day. Given the 12 x conversion factor from mouse to man, a dose of 1–2 mg/kg/day would be predicted to be the protective dose 50 in man.

6. Infection with CMV.

SCID-hu mice implanted with thymus and liver in the kidney capsule were inoculated in the graft with fresh clinical isolates human CMV, strains Toledo (given at $5\times10^6$ PFV) and DK (given at $7\times10^5$) where Toledo was isolated from a diseased fetus (cytomegalic inclusion disease) and DK was isolated from an adult AIDS patient. Both of these strains grew in the implant and at 2, 5, 9 and 15 days post inoculation, two animals were sacrificed and the tissue removed, minced, sonicated and titered for the presence of human CMV by plaque assay on human fibroblasts. For both strains, peaks were observed at about $2\times10^5$ PFU/ml at 9 days for Toledo and at about $2\times10^4$ PFU/ml at 5 days for DK, with the Toledo titer diminishing to about $10^5$ at day 15, while the DK dropped to about 10 PFU/ml by day 15.

Fetal skin (g.w.; __mm$^3$) was implanted on the back in the CB-17 Scid/scid mouse substantially as described. After 24–40 weeks post implant, the skin engrafted mice were inoculated intragraft and intravenously with fresh clinical isolates of human CMV, strains Toledo (given at $5\times10^6$ PFU) and DK (given at $7\times10^5$) and the tissue assayed at 2, 5, 9 and 15 days post inoculation. In skin, both viruses grew with similar qualitative and quantitative characteristics, both peaking at about 5 days at about $6\times10^3$ PFU/ml and diminishing to fewer than about 10 PFU/ml. Particular attention was given to removing the fatty underlayer of mouse tissue adhering to the human skin graft.

In the absence of human tissue capable of maintaining CMV replication, intravenous injection of Toledo ($5\times10^6$) and DK ($7\times10^5$) resulted in the substantial absence of CMV in the peripheral blood within 2 to 4 hours post inoculation.

7. production of human antibodies.

CB-17 scid/scid mice were transplanted with mesenteric lymph nodes into the popliteal fossa region or outer cervical region. An incision is made in the site directly over the fat pad on the back hind leg of the mouse. The main vein that runs vertically up to the trunk that rests on top of the fat pad is cauterized. An incision is made through the fat to expose the popliteal fossa lymph node (LN). The LN is removed and the human tissue is inserted at the same site. Sutures are made to close the dermal incision.

A dose of 50 μg of trinitrophenyl-keyhole limpet hemocyanin (TNP-KLH) combined with specol adjuvant (5 μl TNP-KLH [10 mg/ml] is vortexed with 6 μl specol adjuvant) was injected subcutaneously into the foot pad, where the lymphatic vessels drain into the popliteal fossa lymph node. The graft in one mouse showed appropriate cellularity and was observed to contain a large number of human IgG and IgM positive cells. After 4 days from the immunization, the tissue was harvested, histologic sections prepared and these sections analyzed. The staining procedure is as follows. The immunized human graft is surgically removed from the host and snap frozen in liquid nitrogen. Tissue is sectioned 8 μm thick using a cryostat and placed on glass slides. Tissue is stored if not used promptly at −20° C. The slides are humidified, dried and fixed in acetone for 20 min. Slides are then wet 1× PBS and incubated with trinitrophenyl-conjugated alkaline phosphatase (TNP-AP) diluted in 0.1% BSA/PBS and containing 1% normal human serum. The slides are then incubated for about 2–4 h. The slides are washed 3× in 1x PBS. The development is performed using the substrate solution: naphthol-As-phosphate, fast Blue BB salt dissolved in DMF diluted in 0.05 propandiol buffer, pH 9.75, and 10 mM levamisole-Hcl. The reaction is allowed to proceed for 5–10 min and stopped by submerging the slide in 1x PBS. The slides are then counterstained with hematoxylin for 30 sec, dried and mounted with a coverslip using glycerol/gelatin.

When stained for anti-TNP producing cells, there were several very distinct positive cells. Positive cells show a blue cytoplasmic staining. The staining was shown not to be due to indigenous alkaline phosphatase by the development of the tissue with substrate alone. Blocking of the staining was also shown using 10 μg/ml of TNP-KLH, while 1 ng/ml did not inhibit the cellular staining. The double staining showed human IgM positive cells specific for TNP.

8. Human fetal bone implantation.

Human fetal long bones (17–22 g.w.) of about 1 cm in length (1–2 bones) were transplanted subcutaneously or intraperitoneally into CB-17 scid/scid mice which were preconditioned with 200–300 rads whole body irradiation or were untreated. At different time points after transplantation, bones were taken out and cells recovered from them were stained with either human specific antibody, MEM-43, or mouse specific antibody, Ly.5.1 and analyzed by FACS or cytospin preparations. Sections from the transplants were prepared for routine histology.

Human hematopoiesis was not observed by histology or by cytospin preparations at 2–3 weeks after transplantation. The majority of cells recovered from human bone grafts were positive for MEM-43. Scatter analysis by flow cytometry did not show lymphoid or myeloid populations, suggesting that the majority of cells were non-hematopoietic in origin.

At 4–5 weeks after transplantation, signs of hematopoiesis (i.e., presence of blast cells, immature forms of myelomonocytic cells and erythroblasts) were observed in cytospin preparations in most cases analyzed. The MEM-43 positive cells in these samples showed a scatter profile similar to that of the fetal bone marrow samples. Cells of the myelomonocytic lineage, B cell lineage and the erythroid lineage were shown by immunofluorescent staining with LeuM1 (CD15), CD10 and CD19, and anti-human glycophorin A, respectively. Animals preconditioned with irradiation (200–300 rads) show a significant number of circulating myeloid (CD33) or B lymphoid (CD 19, Ig$^+$) cells in the peripheral blood (0.5–30%).

A. Skin Implantation.

The skin from (1) fetus (16–22 g.w., thigh, scalp and plantar), (2) neonatal skin (foreskin), and (3) adult (trunk) was grown on the back of SCID mice. The subcutaneous tissues of the skin for implantation were removed as much as possible, put as a whole in the mouse skin and stitched. After implantation (2–3 weeks), crust formation on the implanted skin was observed, followed by growth of the implanted skin. Histological examination revealed a very similar structure to normal human skin, i.e., epithelial cells in the epidermis, hair follicles, and adnexal glands and dermal structure.

B. Implantation of placenta.

Small pieces of placental tissue with chorionic villi (16–18 g.w.) were implanted under the kidney capsule of the SCID mouse, as described previously. The growth of placental tissue with cytotrophoblasts was observed 4 weeks after implantation.

C. Implantation of Gut.

Small intestine including appendix from the fetus (16–18 g.w.) was cut into pieces (2×2×3 mm) in cross-section with or without mesenteric tissue, and implanted under the kidney capsule of the SCID mouse. These grafts made cystic structures which contain mucinous fluid inside. The wall of the cyst was lined with the mucosal layer, accompanied with smooth muscle layers similar to those observed in the normal gut.

D. Implantation of Lung.

Small pieces (2×2×2 mm) of fetal lung (18–22 g.w.) were implanted into the SCID mouse (1) under the kidney capsule, (2) in the fourth mammary fat pad, or (3) intraperitoneally. In all cases, rapid growth of implanted lung could be observed. A structure similar to that of fetal lung, including alveolar structure, bronchi and bronchioles with epithelial cells, smooth muscles and soft bones was observed in the grafts 4 weeks after implantation.

E. Implantation of Pituitary.

Fetal pituitary gland (18–22 g.w.) was cut into small pieces and implanted under the kidney capsule of the SCID mouse. After implantation (5–6 weeks), the structure of the implant was very similar to that of the anterior lobe of the pituitary gland with the acinar structure composed of chromophobic, acidophilic and basophilic cells.

F. Implantation of Pancreas.

Fetal pancreatic tissues (18–22 g.w.) were cut into small pieces and implanted under the kidney capsule of the SCID mouse. Pancreatic grafts grew well under the kidney capsule. Histological examination of the grafts (4–6 weeks after implantation) revealed that all the cellular components of pancreatic tissue including acinar glands, ducts with varying size, and well grown islets were of analogous structure to that of normal pancreas. In come cases, a slight fibrotic change between acinus was observed, similar to chronic pancreatitis although the infiltration of mononuclear cells did not accompany the fibrotic change.

It is evident from the above, that by introducing xenogeneic tissue into an immunocompromised host, where the xenogeneic tissue is able to remain viable and functional, a wide variety of advantageous results ensue. One can provide for the testing of efficacy and influence on the immune system of a wide variety of agents, which may include drugs, therapies, pathogens, or the like. These agents may be evaluated for efficacy against diseases, where the xenogeneic tissue may be introduced into the host and infected with the pathogen, followed by determining the effect of an agent on the progress of the pathogen in the xenogeneic tissue or external to the xenogeneic tissue. In addition, one may produce an immune response in xenogeneic B-cells where the resulting B-cells may then be used in substantially conventional manners to any desired epitope.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A chimeric immunocompromised mouse comprising:
   an immunodeficient mouse host at an age of at least neonate, lacking functional syngeneic B and T lymphocytes as a result of a genetic defect in immunoglobulin and T cell receptor gene rearrangement,
   a functional human fetal thymus or progenitor thereof; and
   at least one of human hematopoietic stem cells, immature differentiated human hematopoietic cells or mature human hematopoietic cells derived therefrom as a result of introduction of said human hematopoietic stem cells and human fetal thymus or progenitor thereof into said mouse host.

2. A mouse according to claim 1, wherein said system further comprises dispersed human fetal liver cells, human fetal liver tissue or progenitor thereof.

3. A mouse according to claim 2 wherein said human hematopoietic cells are human fetal cells of from 10 to 24 gestational weeks when introduced and said human fetal thymus organ is comprised of human fetal cells of from about 9 to 24 gestational weeks when introduced.

4. A mouse according to claim 2, wherein said hematopoietic stem cells are from human fetal bone marrow.

5. A mouse according to claim 2 wherein said human hematopoietic cells or human fetal thymus is infected with a virus.

6. A chimeric immunocompromised mouse comprising:
an immunodeficient mouse host at an age of at least neonate, lacking functional syngeneic B and T lymphocytes as a result of a genetic defect in immunoglobulin or T cell receptor gene rearrangement,
at least one functional human fetal organ or progenitor thereof selected from the group consisting of thymus, spleen, bone marrow, lymph node, tonsils, appendix, skin, embryonic yolk sac, fetal liver, and pancreatic tissue; and
human fetal hematopoietic stem cells or mature human hematopoietic cells derived therefrom as a result of introduction of said human hematopoietic stem cells and human fetal organ or progenitor thereof into said mouse host.

7. A mouse according to claim 6, wherein said organ is capable of functioning from the time of introduction into said mouse host for at least three months.

8. A system according to claim 6, wherein said mouse host further comprises at least one additional organ of the hematopoietic system.

9. A mouse according to claim 6, wherein said at least one organ is a human fetal thymus.

10. A system according to claim 9, wherein said mouse host is a scid/scid mouse.

11. A chimeric immunocompromised mouse comprising:
a CB.17 scid/scid mouse host at an age of at least neonate;
a functional human fetal thymus or progenitor thereof; and
at least one of human hematopoietic stem cells; immature hematopoietic cells derived therefrom as a result of introduction of said human hematopoietic stem cells and human fetal thymus or progenitor thereof into said mouse host.

12. A mouse according to claim 11, wherein said mouse host further comprises at least one of fetal lymph node, fetal liver tissue or progenitor thereof.

13. A mouse according to claim 11, wherein said mouse host comprises mature differentiated human hematopoietic cells as a result of maturation in vivo of said human fetal hematopoietic stem cells introduced into said mouse host.

14. A mouse according to claim 13, wherein said differentiated human hematopoietic cells comprise peripheral blood lymphocytes.

15. A mouse according to claim 12, wherein said stem cells are maintained for at least four weeks.

16. A mouse according to claim 12, wherein said human fetal hematopoietic cells or said human fetal thymus is infected with a pathogen.

17. A mouse according to claim 16, wherein said pathogen is a virus.

18. A mouse according to claim 17, wherein said virus is HIV-1.

19. A chimeric immunocompromised mouse comprising:
an immunodeficient mouse host lacking functional syngeneic B and T lymphocytes as a result of a genetic defect in immunoglobulin and T cell receptor gene rearrangement; and
solid functional vascularized human fetal lymphoid organ tissue comprising non-neoplastic cells, wherein said non-neoplastic cells are capable of being infected by a human pathogen.

20. A mouse according to claim 19, wherein said organ tissue is thymus tissue, lymph node tissue, lung tissue or liver tissue.

21. A system according to claim 20, wherein said pathogen is a virus.

22. A system according to claim 21, wherein said virus is HIV.

23. A chimeric immunocompromised mouse comprising:
a CB.17 scid/scid mouse host; and
solid functional vascularized human fetal lymphoid organ tissue comprising non-neoplastic cells wherein,
said non-neoplastic cells are capable of being infected by a human virus.

24. A method for determining the effect of a variation on a diseased state in a chimeric immunocompromised mouse, said method comprising
(a) providing a chimeric immunocompromised mouse, said mouse comprising:
an immunocompromised mouse host at an age of at least neonate, lacking functional syngeneic B and T lymphocytes as a result of a genetic defect in immunoglobulin and T cell receptor gene rearrangement,
functional human fetal thymus or human fetal lymph node tissue, and
at least one of human fetal hematopoietic stem cells, immature differentiated human hematopoietic cells or mature human hematopoietic cells derived therefrom as a result of introduction of said human hematopoietic stem cells and human fetal thymus or human fetal lymph node tissue,
wherein said human fetal thymus or human fetal lymph node tissue is in a diseased state;
(b) subjecting said mouse to said variation; and
(c) determining the effect of said variation on said diseased state.

25. A method according to claim 24, wherein said mouse further comprises:
a second human fetal organ when said disease symptom or indication is associated with such second organ.

26. A method according to claim 25, wherein said mouse host is a CB.17 scid/scid.

27. A method according to claim 24, wherein said variation is administration of a drug.

28. A method according to claim 24, wherein said variation is administration of lymphocytic or myelomonocytic cells specific for said diseased state.

29. A method for producing a chimeric immunocompromised mouse capable of producing mature human hematopoietic cells, said method comprising:
introducing into an immunocompromised mouse host lacking functional syngeneic B or T cells as a result of a genetic defect in immunoglobulin and T cell receptor gene rearrangement, at a site at which human cells can grow, human fetal thymus tissue and at the same or different site, human hematopoietic stem cells.

30. A method according to claim 29, wherein said human hematopoietic stem cells are fetal human hematopoietic stem cells.

31. A method according to claim 30, wherein said mouse host is a CB.17 scid/scid.

32. A method according to claim 31, including the additional step of introducing at least one of human fetal lymph node tissue, human fetal liver tissue, or dispersed human fetal liver tissue.

33. A method according to claim 32, wherein said human fetal cells and tissue are of an age of from about 9 to 24 gestational weeks.

34. A method according to claim 33, wherein said human fetal thymus tissue is of an age of about 9 to 24 gestational weeks, said human fetal lymph node tissue is of an age of greater than about 15 gestational weeks, and said human fetal liver tissue is of an age of from about 10 to 24 gestational weeks.

35. A method for producing a subset of human hematopoietic cells, said method comprising:

(a) introducing human hematopoietic stem cells into a mouse host according to claim 6, with at least one lymphokine for causing differentiation into at least one of the hematopoietic lineages;

(b) maintaining said mouse for sufficient time for said stem cells to differentiate and proliferate to produce cells of said subset; and (c) harvesting said subset of human hematopoietic cells.

* * * * *